US012761111B2

(12) United States Patent
Walz et al.

(10) Patent No.: US 12,761,111 B2
(45) Date of Patent: Oct. 13, 2026

(54) METHOD FOR OPERATING A MEDICAL MICROSCOPE, AND MEDICAL MICROSCOPE ARRANGEMENT

(71) Applicant: Carl Zeiss Meditec AG, Jena (DE)

(72) Inventors: Felicia Walz, Schwäbisch Gmünd (DE); Dominik Scherer, Aalen (DE); Stefan Saur, Aalen (DE); Marco Woerner, Gerstetten (DE); Lars Stoppe, Jena (DE); Christian Platt, Ulm (DE)

(73) Assignee: CARL ZEISS MEDITEC AG, Jena (DE)

( * ) Notice: Subject to any disclaimer, the term of this patent is extended or adjusted under 35 U.S.C. 154(b) by 276 days.

(21) Appl. No.: 18/100,897

(22) Filed: Jan. 24, 2023

(65) Prior Publication Data

US 2023/0316573 A1 Oct. 5, 2023

(30) Foreign Application Priority Data

Jan. 25, 2022 (DE) ..................... 10 2022 200 820.0

(51) Int. Cl.
*G06T 7/80* (2017.01)
*A61B 90/20* (2016.01)
(Continued)

(52) U.S. Cl.
CPC ......... *G01M 11/0264* (2013.01); *A61B 90/20* (2016.02); *A61B 90/94* (2016.02);
(Continued)

(58) Field of Classification Search
CPC .... G01M 11/0264; A61B 90/20; A61B 90/94; A61B 2017/00725; A61B 2090/502;
(Continued)

(56) References Cited

U.S. PATENT DOCUMENTS 5,751,341 A * 5/1998 Chaleki .............. A61B 1/00096 348/E13.058
6,781,682 B1 * 8/2004 Kasai ..................... G02B 7/005 356/138
(Continued)

FOREIGN PATENT DOCUMENTS

CN 111381383 A * 7/2020 ............. G02B 27/62
DE 10355529 A1 * 7/2005 ............. G02B 21/24
(Continued)

*Primary Examiner* — Mohamed K Amara
(74) *Attorney, Agent, or Firm* — NIXON PEABODY LLP; Jeffrey L. Costellia

(57) ABSTRACT

The invention relates to a method for operating a medical microscope, in particular in the field, with an interchange and/or a misalignment of at least one component of the medical microscope being followed by an identification of the interchanged and/or misaligned at least one component, with required adjustment measures and/or calibration measures being determined in automated fashion using the identified at least one interchanged and/or misaligned component as a starting point, and with the determined required adjustment measures and/or calibration measures being carried out. Furthermore, the invention relates to a medical microscope arrangement.

14 Claims, 2 Drawing Sheets

(51) Int. Cl.
*A61B 90/94* (2016.01)
*G01M 11/02* (2006.01)

(52) U.S. Cl.
CPC ...... *G06T 7/80* (2017.01); *G06T 2207/10056* (2013.01); *G06T 2207/20081* (2013.01)

(58) Field of Classification Search
CPC ............. G06T 7/80; G06T 2207/10056; G06T 2207/20081; G06T 7/85; G06T 2207/10012; G06T 2207/20084; G06T 2207/30208; G03B 15/14; G03B 35/08; G03B 35/00; G02B 27/62; G02B 21/0012; G02B 21/24
See application file for complete search history.

(56) References Cited

U.S. PATENT DOCUMENTS

| | | | | |
|---|---|---|---|---|
| 7,848,019 | B2 * | 12/2010 | Jennings | G02B 21/26 359/396 |
| 7,962,033 | B2 * | 6/2011 | Georgiev | G02B 27/0075 396/332 |
| 9,344,650 | B2 | 5/2016 | Winterot et al. | |
| 9,786,053 | B2 * | 10/2017 | Zweig | G06T 7/80 |
| 10,682,039 | B2 | 6/2020 | Muller et al. | |
| 10,989,908 | B2 | 4/2021 | Amthor et al. | |
| 11,006,093 | B1 * | 5/2021 | Hegyi | H04N 13/246 |
| 11,024,019 | B2 | 6/2021 | Amthor et al. | |
| 11,030,776 | B2 * | 6/2021 | Baumgart | G02B 21/361 |
| 12,406,396 | B2 * | 9/2025 | Stopp | G06T 7/80 |
| 12,462,431 | B1 * | 11/2025 | Das | G06T 7/80 |
| 2007/0211243 | A1 * | 9/2007 | Laroche | G02B 21/365 356/243.1 |
| 2011/0043612 | A1 * | 2/2011 | Keller | A61B 1/00165 385/38 |
| 2011/0261324 | A1 * | 10/2011 | Sander | A61B 3/132 351/221 |
| 2014/0340482 | A1 * | 11/2014 | Kanarowski | G02B 21/16 348/46 |
| 2014/0357951 | A1 | 12/2014 | Muller et al. | |
| 2015/0036027 | A1 | 2/2015 | Winterot et al. | |
| 2016/0103309 | A1 * | 4/2016 | Suzuki | G02B 27/145 359/388 |
| 2017/0066131 | A1 * | 3/2017 | Kamikawa | B25J 9/1697 |
| 2017/0285320 | A1 * | 10/2017 | Fletcher | G02B 21/0008 |
| 2018/0364469 | A1 * | 12/2018 | Sakamoto | G02B 21/244 |
| 2018/0373015 | A1 * | 12/2018 | Sakamoto | G02B 21/367 |
| 2019/0282091 | A1 * | 9/2019 | Matsunobu | A61B 3/0033 |
| 2020/0133257 | A1 * | 4/2020 | Cella | G01M 13/045 |
| 2020/0202508 | A1 | 6/2020 | Amthor et al. | |
| 2020/0379236 | A1 | 12/2020 | Amthor et al. | |
| 2021/0157112 | A1 | 5/2021 | Raab et al. | |
| 2021/0169318 | A1 * | 6/2021 | Sorimoto | G02B 21/22 |
| 2021/0235061 | A1 * | 7/2021 | Hegyi | A61B 5/0077 |
| 2022/0061921 | A1 * | 3/2022 | Crawford | A61B 34/20 |
| 2022/0182555 | A1 * | 6/2022 | Kawakami | A61B 1/00039 |
| 2022/0308331 | A1 * | 9/2022 | Kanzaki | G02B 21/244 |
| 2023/0071841 | A1 * | 3/2023 | Ben-Yishai | A61B 1/313 |
| 2023/0090020 | A1 * | 3/2023 | Neta | A61B 3/13 600/249 |
| 2023/0236405 | A1 * | 7/2023 | Walz | G02B 21/0012 359/376 |
| 2023/0390021 | A1 * | 12/2023 | Polchin | A61B 34/30 |
| 2024/0074821 | A1 * | 3/2024 | Kashima | A61F 2/1662 |
| 2025/0104281 | A1 * | 3/2025 | Buschle | A61B 1/000096 |

FOREIGN PATENT DOCUMENTS

| | | | |
|---|---|---|---|
| DE | 10 2013 209 956 | 12/2014 | |
| DE | 10 2013 012 987 | 2/2015 | |
| DE | 10 2018 133 196 | 6/2020 | |
| DE | 10 2019 114 117 | 8/2020 | |
| DE | 102018115824 B4 * | 4/2021 | A61B 5/0077 |
| DE | 10 2019 131 646 | 5/2021 | |
| JP | 2004070036 A * | 3/2004 | |

* cited by examiner

METHOD FOR OPERATING A MEDICAL MICROSCOPE, AND MEDICAL MICROSCOPE ARRANGEMENT

CROSS-REFERENCE TO RELATED APPLICATIONS

The present application claims priority under 35 U.S.C. § 119 to German Patent Application No. 102022200820.0, filed Jan. 25, 2022, the contents of which are incorporated by reference herein in their entirety.

The invention relates to a method for operating a medical microscope, and to a medical microscope arrangement.

One aim of digital visualization in surgery and microsurgery is to display to a surgeon, during an operation, an optimum three-dimensional image of an operation site and, if appropriate, an optimum three-dimensional superimposition of additional information onto a field of view on display devices (e.g., monitors or head-mounted display, etc.) of the medical microscope. The digital calibration data used to optimize the camera images should always be kept current in order to avoid a deterioration in the three-dimensional visualization. An image representation resulting from this, which is perceived as uncomfortable, may lead to the surgeon becoming frustrated and also tired.

To keep the calibration data current, a recalibration of the medical microscope in the field, that is to say at an application or operation location of the medical microscope, for example carried out by a service technician, is mandatory. The reason for this being that the calibration data are valid for a specific state of an imaging optical unit and, optionally, further optical components of the medical microscope. An interchange of a component of the medical microscope or arising vibrations and displacements (misalignment) of the components connected therewith however cause a deterioration in the effect of the calibration data, or even render the latter invalid. Depending on the type of effect, a more or less comprehensive recalibration (with a fewer or greater number of operating points) must be carried out in this case.

Methods for the extrinsic recalibration of cameras of stereoscopic surgical microscopes in the field with the aid of a defined calibration object (which is also referred to as target) and for various operating points are known. Such a calibration method is known from DE 10 2019 131 646 A1, for example. To simplify the optical calibration of optical observation equipment, a stand for an optical observation unit comprising a calibration object arranged directly on the stand in a fixed location is used in that case. Moreover, optical observation equipment, which comprise such a stand and an optical observation unit connected to the stand, a method for calibrating such optical observation equipment, and a computer program are described. A method for calibrating a digital microscope is further known from DE 10 2013 012 987 A1.

The invention is based on the object of developing a method for operating a medical microscope and a medical microscope arrangement, by means of which a recalibration can be carried out more easily, in particular more efficiently, in particular in the field, following an interchange of one or more components of the medical microscope and/or a misalignment (an unwanted change of pose) of one or more components. In this case, a misalignment refers in particular to deviation of a pose (position and/or orientation) of a component from a target pose, for example because the pose of the component has changed as a result of a vibration or other influences (influence of temperature, mechanical tolerances, etc.).

According to the invention, the object is achieved by a method having the features of patent claim 1, and a medical microscope arrangement having the features of patent claim 1. Advantageous configurations of the invention emerge from the dependent claims.

One of the basic concepts of the invention lies in the fact that an interchange by a service technician and/or a misalignment, in general a change, of at least one component of the medical microscope, for example a varifocal objective or a camera, is followed by the interchanged and/or misaligned at least one component being identified. In particular, this should ensure that all interchanged and/or misaligned components are known to the subsequent measures and are able to be taken into account. In this case, an interchange and/or a misalignment should, in general terms, in particular denote a change in at least one component. Required adjustment measures and/or calibration measures are determined in automated fashion using the identified at least one interchanged and/or misaligned component as a starting point. In particular, this is implemented by means of a data processing device which may be part of the medical microscope or else may be formed separately therefrom as a part of the medical microscope arrangement. The determined required adjustment measures and/or calibration measures are subsequently carried out. The automated determination of the required adjustment measures and/or calibration measures allows a service technician in the field to be provided with valuable information for assisting with the service operation. This can avoid errors in the recalibration and an incomplete recalibration. Further, it is possible in particular to reduce the time required to carry out the recalibration since the recalibration can be restricted to the required adjustment measures and/or calibration measures.

In particular, a method for operating a medical microscope, in particular in the field, is provided, with an interchange and/or a misalignment of at least one component of the medical microscope being followed by an identification of the interchanged and/or misaligned at least one component, with required adjustment measures and/or calibration measures being determined in automated fashion using the identified at least one interchanged and/or misaligned component as a starting point, and with the determined required adjustment measures and/or calibration measures being carried out.

Further, a medical microscope arrangement, in particular, is developed, comprising a medical microscope with storable calibration data and a data processing device, the data processing device being configured, following an interchange and/or a misalignment of at least one component of the medical microscope, to identify the interchanged and/or misaligned at least one component and/or to receive identifying information in relation to the interchanged and/or misaligned at least one component, to determine required adjustment measures and/or calibration measures in automated fashion using the identified at least one interchanged and/or misaligned component as a starting point, and to cause the determined required adjustment measures and/or calibration measures to be carried out.

One of the advantages of the method and the medical microscope arrangement is that these consider the challenges arising during a calibration in the field. Thus, calibration data of medical microscopes are usually very comprehensive and, for example, further calibration steps are required in addition to an extrinsic calibration of cameras of the medical microscope in order to be able to restore a complete calibration data set. While the required equipment and processes for complex calibration are available at the manufacturer, it generally is very difficult for a service technician to carry out an optimal recalibration in the field, that is to say at the application or operation location of the medical microscope. The same applies to required adjustment measures. Reasons for this include, in particular, that the technician firstly lacks knowledge about the required measures dependent on the implemented service operation and secondly lacks tools optimized for the overall process.

A further advantage is that, moreover, a downtime and, therewith, a duration of the service operation on the medical microscope can be minimized.

A medical microscope is a surgical microscope in particular. However, a medical microscope may also be a microscope used for medical examinations and/or for diagnostic purposes, for example in the field of ophthalmology or in other fields. A medical microscope arrangement is a surgical microscope arrangement in particular. The medical microscope is a digital microscope and/or a stereoscopic medical microscope in particular. One component of the medical microscope is an optical component in particular, that is to say in particular a component that influences an optical imaging and/or capture procedure in the medical microscope. In a manner known per se, the medical microscope comprises, in particular, a control device for controlling the components, an input device for operation, and a display device for displaying captured image representations.

The data processing device may also be part of the medical microscope, for example part of a control device of the medical microscope. However, in principle the data processing device may also be formed separately from the medical microscope, for example as a desktop, laptop or tablet computer, or else in a cloud-based solution.

The calibration measures may in particular comprise one or more of the following measures: an extrinsic calibration of cameras, an intrinsic calibration of cameras, a distortion correction, a trimming correction (camera vignetting and/or illumination geometry), a chromatic aberration correction, an offset correction, a rotation correction, etc.

Parts of the medical microscope arrangement, in particular the data processing device, can be designed, either individually or together, as a combination of hardware and software, for example as program code that is executed on a microcontroller or microprocessor. However, provision can also be made for parts to be designed as application-specific integrated circuits (ASICs) and/or field-programmable gate arrays (FPGAs), either on their own or in combination.

In an embodiment, provision is made for a calibration object with two-dimensional features and/or three-dimensional features to be used to carry out the adjustment measures and/or calibration measures and for said calibration object to be arranged in a capture region of the medical microscope to this end. This can simplify the recalibration since, in particular, all required adjustment measures and/or calibration measures can be carried out with the aid of the one calibration object. In particular, this can avoid changing calibration objects for different measures. In particular, the calibration object is a combined calibration object, which combines a two-dimensional calibration object with two-dimensional features and a three-dimensional calibration object with three-dimensional features.

Therefore, a calibration object comprising two-dimensional features and three-dimensional features is also developed, with the two-dimensional features comprising a plane with two-dimensional structures, and the three-dimensional features comprising a plane that is inclined in relation to the plane with the two-dimensional structures. By way of example, the two-dimensional structures may comprise a checkerboard pattern, ChArUco structures, a grid with anchor points, and/or similar, uniquely identifiable geometric structures. The three-dimensional features may also be designed completely differently.

In an embodiment, provision is made for the identification of the interchanged and/or misaligned at least one component to be implemented at least partially manually, with at least one information item identifying the at least one interchanged and/or misaligned component being collected to this end by means of an operating device by way of a manual input. As a result, the interchanged and/or misaligned at least one component can be identified directly by a service technician by way of a manual input. The operating device is, in particular, an operating device of the data processing device and/or medical microscope. By way of example, provision can be made in this context for serial numbers of the interchanged and/or misaligned at least one component to be collected. However, provision can also be made for the interchanged and/or misaligned at least one component to be identified on the operating device with the aid of selectable symbols.

In an embodiment, provision is made for the identification of the interchanged and/or misaligned at least one component to be implemented at least partially in automated fashion, with at least one information item identifying the at least one interchanged and/or misaligned component being read and/or retrieved to this end out of the interchanged and/or misaligned component and/or from at least one control device of the medical microscope and/or from a service database. As a result, the identification can be implemented in automated fashion. As a result, the method can be implemented in accelerated fashion and (manual) incorrect inputs can be reduced or even prevented. By way of example, the identifying information can be a serial number or a unique identification number, which are retrieved and/or read directly from the interchanged and/or misaligned at least one component and/or from a control device which controls the interchanged and/or misaligned at least one component, and/or from a service database in which a service task to be carried out, which describes the components to be interchanged and/or the misaligned components, is stored. By way of example, the identifying information can be retrieved and/or read from an EEPROM or flash memory. In particular, the medical microscope is configured to recognize whether components were interchanged and/or have become misaligned. Following an interchange, this can be implemented, for example, by a comparison between a serial number and/or a unique identification number, which is stored in a memory of the medical microscope for the (old) component, and a read and/or retrieved serial number and/or unique identification number of the interchanged (new) component. If the comparison yields that a component has been interchanged, the identifying information is read and provided.

In an embodiment, provision is made for the required adjustment measures and/or calibration measures to be at least partially determined by means of a lookup table, with adjustment measures and/or calibration measures that are required in each case following the interchange and/or misalignment being stored in the lookup table for interchangeable and/or adjustable components of the medical microscope. As a result, the required adjustment measures and/or calibration measures can be determined in a particularly time-saving and efficient manner. By way of example, the lookup table may be stored in a memory of the data processing device. Entries in the lookup table are or were determined, in particular, by means of expert knowledge and/or empirical trials and/or simulations. In this case, provision can be made for this to be followed by an optimization of the entries by means of statistical evaluations. In particular, every possible service operation is reconstructed and/or simulated in order to determine which adjustment measures and/or calibration measures are required. To this end, effects arising by the interchange of the at least one component, in particular, are determined by expert knowledge and, if required, by empirical trials and/or simulations. The required adjustment measures and/or calibration measures are determined on the basis thereof. In the process, the measures may also be trialed, in particular, and the effectiveness and/or necessity thereof may be evaluated statistically. The determined measures are then stored in the lookup table for the respective interchanged and/or misaligned at least one component that is the focus of the service operation or for combinations of components.

By way of example, if a camera of the medical microscope is interchanged, consideration of the "camera interchange" scenario yields that the interchanged camera initially needs to be adjusted mechanically with the aid of the (combined) calibration object and subsequently still needs to be (digitally) calibrated with the aid of the calibration object. In particular, this only needs to be implemented for one operating point (magnification and focus). Further empirical trials and/or a simulation are not required any more since these measures can be derived from the expert knowledge. Naturally, empirical trials and/or simulations may nevertheless be carried out. By way of example, the following measures are then stored in the lookup table: arrange calibration object in the capture region of the medical microscope, mechanically adjust the interchanged camera (focus), mechanically adjust the camera (x/y-direction and rotation), (digital) calibration (x/y-direction and rotation).

By way of example, if a varifocal objective of the medical microscope is interchanged, a consideration of the "varifocal objective interchange" scenario yields that offset values that serve for an image stabilization for travel of the varifocal objective have to be updated (recalibrated). The offset values are usually available for a given number of support points/varifocal objective positions. Empirical trials are used to determine the number of support points at which the offset values need to be redetermined and at which points an interpolation of the offset value is sufficient for a given accuracy. By way of example, if offset values from an initial assembly of the (old) varifocal objective are available for ten positions and the trials yield that a remeasurement is only required for every second position since the intermediate values can be interpolated, this yields that five positions have to be remeasured by calibration measures. By way of example, the following measures are then stored in the lookup table: arrange calibration object in the capture region of the medical microscope (if this has not yet been implemented), home in on the five positions of the varifocal objective and measure the respective offset values.

Provision can be made for an interchange and/or misalignment of a plurality of components to be followed by the combination of measures for these components. By way of example, an appropriate logic may be stored to this end. If, for example, both a camera and a varifocal objective are interchanged using the above-described examples as a starting point, it is possible to at least partially combine the adjustment measures and/or calibration measures so that a number and/or scope of the measures can be reduced.

In an embodiment, provision is made for the required adjustment measures and/or calibration measures to be at least partially retrieved from a database, with adjustment measures and/or calibration measures that are required in each case following the interchange and/or misalignment being stored in the database for interchangeable and/or adjustable components of the medical microscope. The entries in the database can be generated in a manner analogous to what was described above for the lookup table. By way of example, the database may be stored in a memory of the data processing device. However, in principle the database may also be stored on a central or decentralized (e.g., cloud-based) server, with, by way of a communications link configured to this end, the database being retrieved from the central server when required by means of the data processing device.

In an embodiment, provision is made for the required adjustment measures and/or calibration measures to be at least partially determined by means of a trained artificial intelligence method. As a result, it is possible, in particular, to also determine the measures for combinations of interchanged and/or misaligned components that are not stored in a lookup table or database, or for combinations for which no measures were determined in advance. In particular, the measures are estimated by means of the trained artificial intelligence method. Methods known per se, for example pattern recognition methods and artificial neural networks, can be used to this end. In particular, the machine learning method is trained for a multiplicity of scenarios, that is to say for a multiplicity of interchanged and/or misaligned components and the combinations thereof. In this case, respective pairs of a component or a combination of a plurality of components and adjustment measures and calibration measures assigned thereto, in particular, are generated and used as training data. The training data can be generated analogously, by definition on the basis of expert knowledge, by empirical trials and/or by simulation, as has already been described above for the lookup table and the database. The artificial intelligence method, for example a suitable neural network, is then trained using these training data. A structure and parameters of the trained artificial intelligence method, for example the trained neural network, are then stored in a memory of the data processing device such that the trained artificial intelligence method can subsequently be provided and used by the data processing device.

In an embodiment, provision is made for the determined required adjustment measures and/or calibration measures to be displayed by means of a display device (for example by means of a (computer) monitor or a head-mounted display). As a result, a service technician can be provided with instructions regarding the measures to be carried out following the interchange and/or misalignment of the at least one component. In this context, provision can for example be made for the service technician to be guided step by step through the required adjustment measures and/or calibration measures with the aid of a graphical user interface, and for the service technician to receive detailed instructions as a result. Such instructions can also be enriched with multimedia content, for example explanatory videos and/or voice information. By way of example, such instructions can be prepared for all possible adjustment measures and/or calibration measures and can be stored in the data processing device, and so said instructions can be retrieved and displayed according to requirements.

In an embodiment, provision is made for at least some of the determined required calibration measures to be carried out in automated fashion. This can unburden a service technician. Further, servicing or repair work and the subsequent implementation of the required adjustment measures and/or calibration measures may optionally also be carried out without a service technician by a user of the medical microscope themselves. In that case, the calibration measures are carried out, in particular, by automated control and/or closed-loop control of actuator systems of the medical microscope for the purposes of homing in on required operating points, an implementation of required measurements, and a subsequent determination and adjustment of calibration data. In this case, the calibration measures in particular also comprise an adjustment of calibration data for signal or image processing of a camera system of the medical microscope.

In an embodiment, provision is made for at least one calibration object to be arranged in automated fashion in a capture region by means of an actuator system in order to carry out the determined required adjustment measures and/or calibration measures. As a result, the arrangement of the calibration object in the capture region can also be carried out in automated fashion. In particular, the at least one calibration object is a calibration object having both two-dimensional features and three-dimensional features.

Alternatively or additionally, provision can also be made for the medical microscope to be controlled so that a capture region of the medical microscope captures at least one calibration object in order to carry out the determined required adjustment measures and/or calibration measures. By way of example, a (robotic) actuator system of a stand of the medical microscope can be controlled in such a way that a calibration object arranged at the medical microscope, for example at the stand of the medical microscope, is captured by the capture region of the medical microscope as a result of arranging/aligning the medical microscope.

In an embodiment, provision is made for the required adjustment measures and/or calibration measures to be combined and/or optimized with one another in the case of a plurality of interchanged and/or misaligned components, in order to minimize a number and/or a scope of the measures. This can reduce the time required to carry out the adjustment measures and/or calibration measures. The combination allows a reduction of measures which would otherwise be carried out twice or whose operating points partially overlap. A number of operating points required for the calibration can likewise be reduced within the scope of the optimization, for example because calibration data can be obtained by interpolation and the associated operating points therefore do not have to be measured. Provision can likewise be made for an optimal sequence for homing in on the individual operating points to be determined and provided within the scope of the combination and/or optimization, the optimal sequence for example having a minimum value for an accumulated travel during the adjustment of the operating points or the shortest duration.

In an embodiment, provision is made for data for anticipatory servicing to be collected and/or recorded in the medical microscope, with data for determining and/or optimizing the determination of the adjustment measures and/or calibration measures being evaluated, said data having been collected before, during and/or after the interchange and/or the misalignment of the at least one component. If these data are collected for a multiplicity of medical microscopes in the field, optimal measures can be identified on the basis of these data. As a result, optimized adjustment measures and/or calibration measures can be obtained. In particular, an effect of the interchange and/or the misalignment and the subsequent adjustment measures and/or calibration measures can be assessed and taken into account when defining the respective adjustment measures and/or calibration measures in the lookup table and/or in the database, or when training the artificial intelligence.

In an embodiment, provision is made for a respective state of the medical microscope to be captured before and after the interchange and/or misalignment, with associated image representations of at least one calibration object being captured by means of at least one capture device of the medical microscope and with the required adjustment measures and/or calibration measures being determined by means of a trained artificial intelligence method, with the states captured before and after the interchange and/or the misalignment and the associated captured image representations being taken into account. The artificial intelligence method is learned in advance, with training data being generated by virtue of the calibration data determined by the calibration being systematically modified and respective image pairs (before and after the interchange or misalignment) being captured. This can be implemented either manually on the medical microscope or by simulation. The artificial intelligence method, for example a neural network, is trained with the aid of the image pairs generated in this way and the respective modification of the calibration data accompanying this (basic truth). Subsequently, a structure and parameters of the trained artificial intelligence method can be stored for application purposes in a memory of the data processing device, and so the trained method can then be provided for application purposes. This embodiment can be used, in particular, also in assistive fashion or in combination with the other described embodiments.

Further features relating to the configuration of the medical microscope arrangement arise from the description of configurations of the method. Here, the advantages of the medical microscope arrangement are in each case the same as in the configurations of the method.

The invention is explained in greater detail below on the basis of preferred exemplary embodiments with reference to the figures. In the figures.

Figure 1:
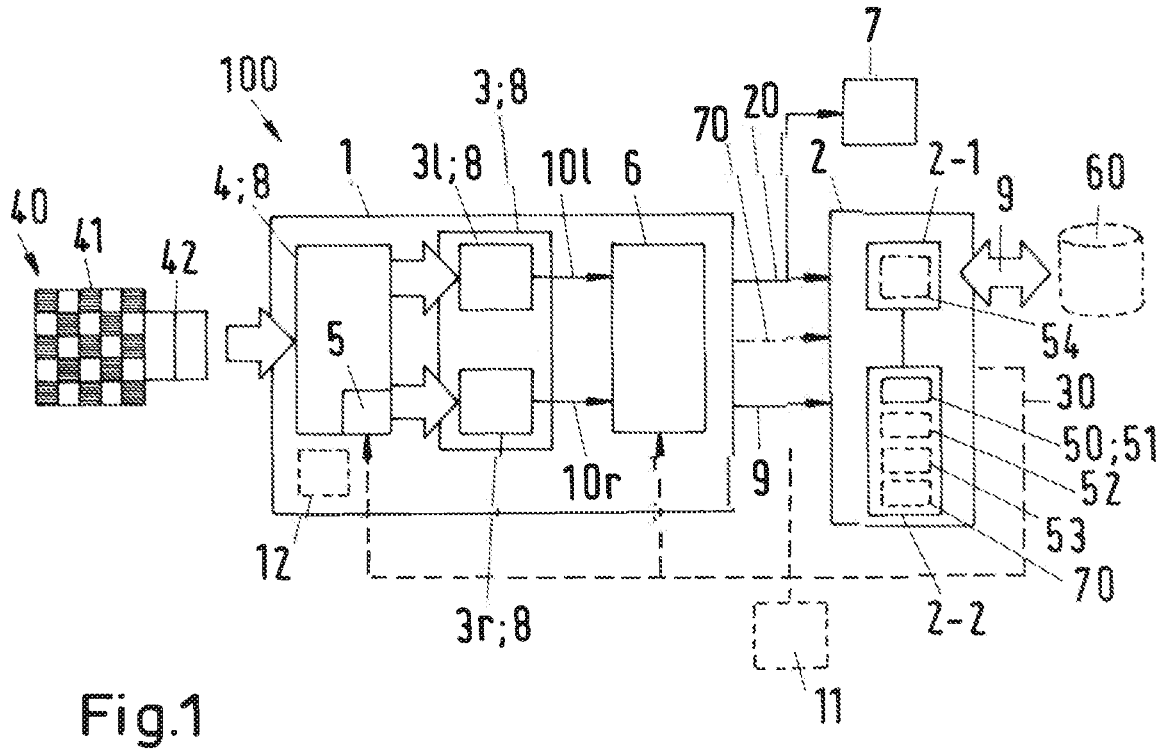
FIG. 1 shows a schematic representation of an embodiment of the medical microscope arrangement.

FIG. 1 shows a schematic representation of an embodiment of a medical microscope arrangement 100. The medical microscope arrangement 100 comprises a medical microscope 1, in particular a digital and stereoscopic microscope, for example a surgical microscope, and a data processing device 2. The method described in this disclosure is explained in more detail below on the basis of the medical microscope arrangement 100.

The medical microscope 1 comprises a stereo camera system 3, which comprises a left camera 31 and a right camera 3*r*. The cameras 31, 3*r* capture a capture region imaged by way of an imaging optical unit 4 (only illustrated schematically here) of the medical microscope 1. To correct errors in an adjustment in particular, calibration data 30, for example for an optical unit actuator system 5 configured to change properties of the imaging optical unit 4, can be stored for the imaging optical unit 4.

The imaging optical unit 4 or parts thereof and the cameras 3l, 3r of the stereo camera system 3 form components 8 of the medical microscope 1. In particular, these components 8 are interchangeable, that is to say the components 8 can be swapped by way of a service operation, for example if said components are defective and no longer operate correctly. The term interchangeable should in particular also comprise a component 8 being removed from the medical microscope 1, being cleaned and/or serviced, and subsequently being reinstalled in the medical microscope 1.

Further, the medical microscope 1 comprises a signal processing device 6, which processes a raw signal 10l provided by an image sensor of the left camera 3l and a raw signal 10r provided by an image sensor of the right camera 3r and which generates and provides image representations 20 from the raw signals 10l, 10r. By way of example, the image representations 20 can be displayed on at least one display device 7, for example one or more (computer) monitors or a head-mounted display (HMD), which in particular may also be part of the medical microscope 1. The signal processing may comprise, in particular, a picture element-dependent modification of a brightness and/or a generation of an offset and/or a rotation about an image center (or any other point), and further manipulations (filtering, color correction, etc.). Calibration data 30 for correcting the raw signals 10l, 10r may be stored in the signal processing device 6. Provision can also be made for the calibration data 30 to be stored only in the image processing device 6.

The data processing device 2 comprises a computing device 2-1, for example a microprocessor or microcontroller, and a memory 2-2. The data processing device 2 may also be a part of the medical microscope 1 and, for example, may be integrated in a control device (not shown here) of the medical microscope 1.

The data processing device 2 is configured, following an interchange and/or a misalignment of at least one component 8 of the medical microscope 1, to identify the interchanged and/or misaligned at least one component 8 and/or to receive identifying information 9 in relation to the interchanged and/or misaligned at least one component 8, to determine required adjustment measures 50 and/or calibration measures 51 in automated fashion using the identified at least one interchanged and/or misaligned component 8 as a starting point, and to cause the determined required adjustment measures 50 and/or calibration measures 51 to be carried out. The adjustment measures 50 and/or calibration measures 51 are then carried out in a manner known per se.

Provision can be made for a calibration object 40 with two-dimensional features 41 and three-dimensional features 42 to be used to carry out the adjustment measures 50 and/or calibration measures 51 and for said calibration object to be arranged in a capture region of the medical microscope 1 to this end. An embodiment of such a calibration object 40 is shown in exemplary fashion in FIGS. 2A and 2B, which will be described below.

Provision can be made for the identification of the interchanged and/or misaligned at least one component 8 to be implemented at least partially manually, with at least one information item 9 identifying the at least one interchanged and/or misaligned component being collected to this end by means of an operating device 11 by way of a manual input. By way of example, the operating device 11 may comprise a display and input means (neither of which are shown here). In this case, the operating device 11 may also be part of the medical microscope 1 or data processing device 2. Following the interchange and/or the misalignment of the at least one component 8, a service technician can provide the at least one identifying information item 9 by way of a manual input on the operating device 11. The at least one identifying information item 9 may for example comprise a unique serial number and/or identification number of the at least one interchanged and/or misaligned component 8. The manual input may also comprise scanning a barcode or QR code arranged on the interchanged component 8. In this case, this is already implemented before the component 8 is interchanged, in particular.

Provision can be made for the identification of the interchanged and/or misaligned at least one component 8 to be implemented at least partially in automated fashion, with at least one information item 9 identifying the at least one interchanged and/or misaligned component 8 being read and/or retrieved to this end out of the interchanged and/or misaligned component 8 and/or from at least one control device of the medical microscope 1 and/or from a service database 60. Reading and/or retrieving the at least one interchanged and/or misaligned component 8 is implemented, for example, by way of a communications line or a bus system, by means of which the components 8 of the medical microscope 1 are connected to one another and to the at least one control device.

Provision can be made for the required adjustment measures 50 and/or calibration measures 51 to be at least partially determined by means of a lookup table 52, with adjustment measures 50 and/or calibration measures 51 that are required in each case following the interchange and/or misalignment being stored in the lookup table 52 for interchangeable and/or adjustable components 8 of the medical microscope 1. The lookup table 52 is stored in the memory 2-2 of the data processing device 2. The data processing device 2 then retrieves the required adjustment measures 50 and/or calibration measures 51 from the lookup table 52 on the basis of the identified interchanged and/or misaligned components 8.

Provision can be made for the required adjustment measures 50 and/or calibration measures 51 to be at least partially retrieved from a database 53, with adjustment measures 50 and/or calibration measures 51 that are required in each case following the interchange and/or misalignment being stored in the database 53 for interchangeable and/or adjustable components 8 of the medical microscope 1. The database 53 can be stored in the memory 2-2 of the data processing device 2. Alternatively or additionally, the required adjustment measures 50 and/or calibration measures 51 may also be at least partially retrieved from an (external) service database 60. In principle, the procedure is the same as already described above for the example of the lookup table 52.

Provision can be made for the required adjustment measures 50 and/or calibration measures 51 to be at least partially determined by means of a trained artificial intelligence method 54. The trained artificial intelligence method 54 is provided by means of the data processing device 2 and estimates the required adjustment measures 50 and/or calibration measures 51 using the identified interchanged and/or misaligned components 8 as a starting point. By way of example, a trained neural network can be used as trained artificial intelligence method 54.

In particular, provision is made for the determined required adjustment measures 50 and/or calibration measures 51 to be displayed by means of the display device 7. In particular, this is implemented within the scope of step-by-step instructions, which provide a service technician with detailed instructions for the individual measures 50, 51. By way of example, a graphical user interface can be displayed on the display device 7 to this end, the individual instructions being provided on said display device in graphical and/or text form.

Provision can be made for at least some of the determined required calibration measures 51 to be carried out in automated fashion. This comprises those calibration measures 51, in particular, which relate to the signal processing of the captured raw signals 10*l*, 10*r* in the signal processing device 6. By way of example, these calibration measures 51 may relate to an extrinsic and/or intrinsic calibration of the cameras 3*l*, 3*r* (camera projection matrices), an offset (x/y-offset), and/or a rotation, a distortion, trimming of the brightness (camera vignetting and/or illumination geometry), and/or a chromatic aberration. The calibration measures 51 to this end are known per se, and are therefore not described in more detail here.

Provision can be made for at least one calibration object 40 to be arranged in automated fashion in a capture region by means of an actuator system 12 in order to carry out the determined required adjustment measures 50 and/or calibration measures 51. To this end, the actuator system 12 is controlled accordingly. To this end, the actuator system 12 for example receives an appropriate control signal, which causes the actuator system 12 to bring the at least one calibration object 40 from a stored position to a measurement position. By way of example, the control signal may be generated by the data processing device 2 or a control device (not shown here) of the medical microscope 1 and be fed to the actuator system 12. In this context, provision may also be made for a distance between calibration object 40 and an objective of the medical microscope 1 (z-direction) to be able to be varied or set by means of the actuator system 12.

Provision can be made for the required adjustment measures 50 and/or calibration measures 51 to be combined and/or optimized with one another in the case of a plurality of interchanged and/or misaligned components 8, in order to minimize a number and/or a scope of the measures 50, 51. This can be implemented when the method is carried out. However, provision can also be made for the combination and/or optimization to be carried out when generating the lookup table 52 and/or database 53, and/or when training the artificial intelligence method 54. This is advantageous in that computational power and memory requirements are not restricted by the data processing device 2.

Provision can be made for data 70 for anticipatory servicing to be collected and/or recorded in the medical microscope 1, with data 70 for determining and/or optimizing the determination of the adjustment measures 50 and/or calibration measures 51 being evaluated, said data having been collected before, during and/or after the interchange and/or the misalignment of the at least one component 8. In particular, the data 70 are collected by means of sensors (not shown here) of the medical microscope 1 configured to this end. The determination and/or optimization is implemented, in particular, by means of a central server (not shown here) on the basis of data 70 which were collected by a multiplicity of medical microscopes 1 in the field.

Provision can be made for a respective state of the medical microscope 1 to be captured before and after the interchange and/or misalignment, with associated image representations 20 of at least one calibration object 40 being captured by means of at least one capture device of the medical microscope 1 and with the required adjustment measures 50 and/or calibration measures 51 being determined by means of a trained artificial intelligence method 54, with the states captured before and after the interchange and/or the misalignment and the associated captured image representations 20 being taken into account. At least one information item 9 identifying the at least one interchanged and/or misaligned component 8 and the image representations 20 captured beforehand and afterwards are fed to the trained artificial intelligence 54, for example a trained neural network, as input data. Using this as a starting point, the trained artificial intelligence method 54 estimates the required adjustment measures 50 and/or calibration measures 51.

Figure 2A:
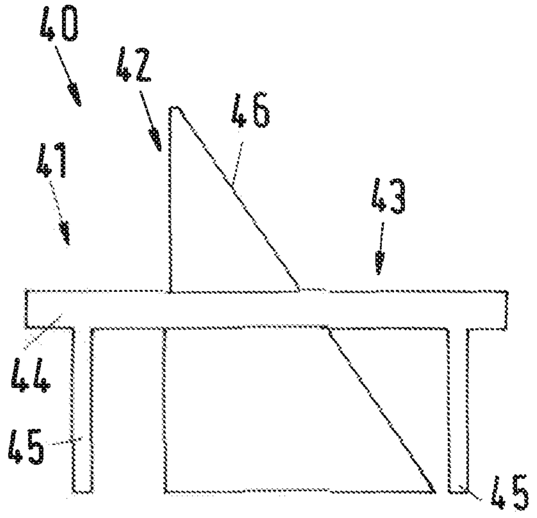
FIG. 2A shows a schematic representation of an embodiment of the calibration object with two-dimensional features and three-dimensional features in a side view.
Figure 2B:
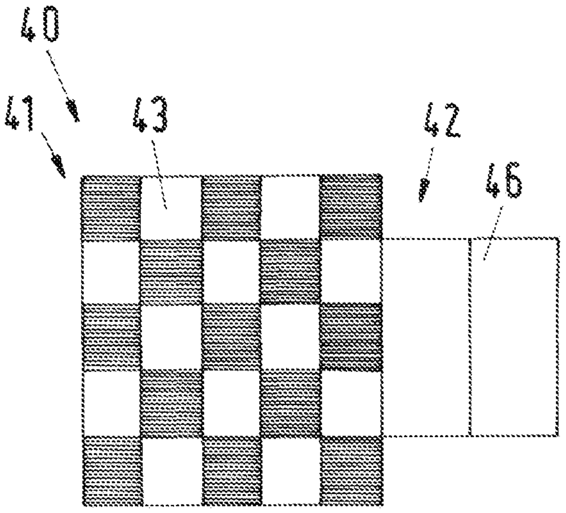
FIG. 2B shows a schematic representation of an embodiment of the calibration object with two-dimensional features and three-dimensional features in a plan view.

FIGS. 2A and 2B show a schematic representation of an embodiment of the calibration object 40 with two-dimensional features 41 and three-dimensional features 42 in a side view FIG. 2A and in a plan view FIG. 2B, which corresponds to a view of the calibration object 40 that would be captured by the medical microscope 1. The two-dimensional features 41 form a two-dimensional calibration object in particular. The latter comprises a checkerboard pattern 43 on a top side. As an alternative or in addition to the checkerboard pattern 43 shown in exemplary fashion, provision can also be made of ChArUco structures, a grid with anchor points, or any other uniquely identifiable features. In the embodiment shown, the checkerboard pattern 43 is arranged in exemplary fashion on a plane 44 which is arranged on a plurality of support legs 45. Other suitable support structures, for example a base or a cube, etc., can also be provided as an alternative to the support legs 45. With the aid of the checkerboard pattern 43 it is possible, in particular, to determine an offset (e.g., x/y-direction) and a rotation between the raw data or image representations captured by the cameras of the stereo camera system 3, and also a distortion. The three-dimensional features 42 form a three-dimensional calibration object which has a triangular, in particular wedge-like shape with a plane 46 that is inclined in relation to the plane 44, with the result that different distances (e.g., z-direction) can be captured and measured at the same time. In particular, provision is made in the case of an arrangement in the capture region of the medical microscope 1 for vertical lines running along a depth of field range, vertically and horizontally running lines and/or checkerboard patterns and/or other black/white patterns running uniformly along the depth of field range to be formed on the inclined plane 46.

Figure 3:
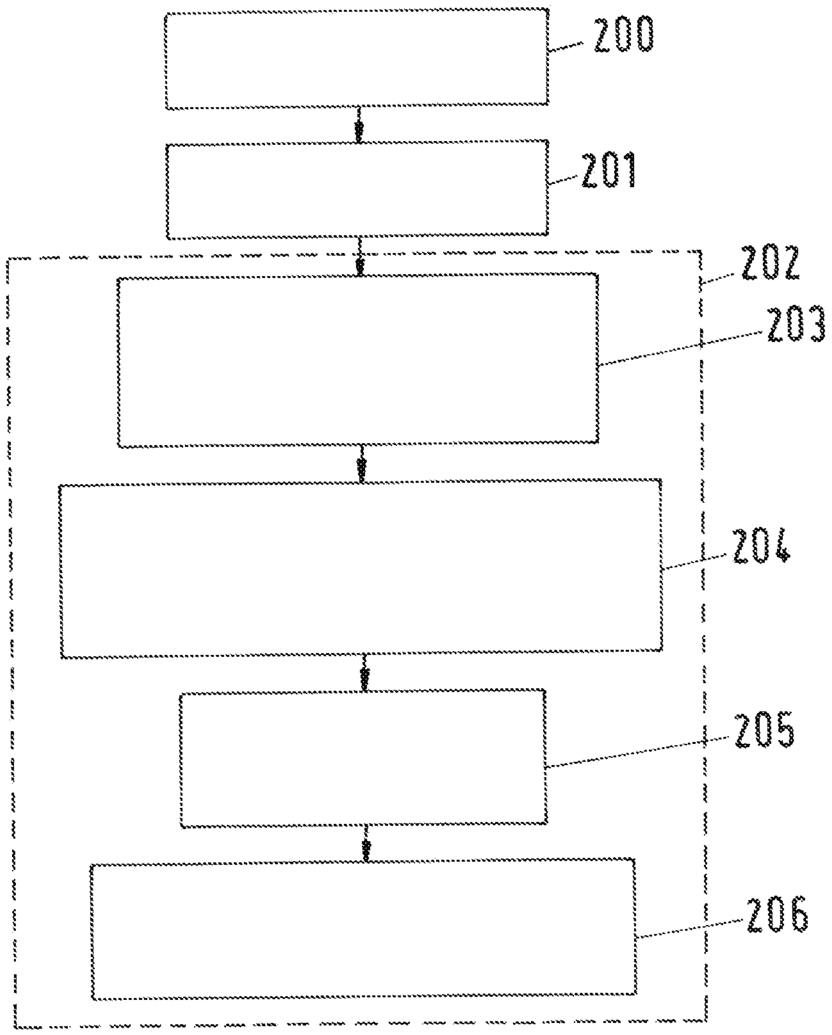
FIG. 3 shows a schematic flowchart of an embodiment of the method for operating a medical microscope.

FIG. 3 shows a schematic flowchart of an embodiment of the method for operating a medical microscope 1.

In a method step 200, a component, for example a varifocal objective, of the medical microscope 1 is swapped by a service technician. Alternatively or additionally, a misalignment of at least one component may also be present.

The readjustment and/or recalibration is started by the service technician in a method step 201. By way of example, this is implemented by an appropriate input on the data processing device of the medical microscope arrangement.

Instructions for the readjustment and/or recalibration by method steps 203-206 is provided in a method step 202.

In a method step 203, the interchanged and/or misaligned at least one component, the varifocal objective in this example, is identified. In this case, provision can be made for the identification of the interchanged and/or misaligned at least one component to be implemented at least partially manually, as has already been described above. Alternatively or additionally, provision can be made for the identification of the interchanged and/or misaligned at least one component to be implemented at least partially in automated fashion, as has likewise already been described above. In this example, information identifying the varifocal objective is available, in particular, following method step 203.

In a method step 204, required adjustment measures and/or calibration measures are determined in automated fashion using the identified at least one interchanged and/or misaligned component as a starting point, using the varifocal objective as a starting point in this example, as has already been described above with respect to FIG. 1. Here, the fact that five operating points with different magnification settings have to be homed in on in order to compensate a varifocal objective travel that has been changed by the interchange was determined in this example, with only calibration measures having to be implemented to this end.

The required calibration measures are displayed on a display device in method step 205. This can be implemented in a graphically configured form (pictograms, flowcharts, animations, etc.) in particular.

In this way, step-by-step instructions for the service technician for homing in on the individual operating points and for carrying out the required calibration measures are implemented in method step 206. Once the calibration measures have been implemented, calibration data generated in the process, relating to the varifocal objective in this example, are stored in a memory of the medical microscope provided to this end, and subsequently serve for the (digital) correction.

If other components require adjustment measures, instructions for the service technician for carrying out the adjustment measures are displayed on the display device in an analogous fashion.

As a result of the method, the service technician can be efficiently guided through the required adjustment measures and/or calibration measures. This can reduce outlay and duration, and can consequently save costs.

LIST OF REFERENCE SIGNS

1 Medical microscope
2 Data processing device
2-1 Computing device
2-2 Memory
3 Stereo camera system
**3*l*** Left camera
**3*r*** Right camera
4 Imaging optical unit
5 Optical unit actuator system
6 Signal processing device
7 Display device
8 (Interchanged) component
9 Identifying information
**10*l*** Raw signal (left camera)
**10*r*** Raw signal (right camera)
11 Operating device
12 Actuator system
20 Image representation
30 Calibration data
40 Calibration object
41 Two-dimensional features
42 Three-dimensional features
43 Checkerboard pattern
44 Plane
45 Support leg
46 Inclined plane
50 Adjustment measure
51 Calibration measure
52 Lookup table
53 Database
54 Trained artificial intelligence
60 Service database
70 Data
100 Medical microscope arrangement
200-206 Method steps of the method

The invention claimed is:

1. A method for operating a medical microscope, the method comprising:

identifying an interchanged and/or misaligned at least one component of the medical microscope, the at least one component being at least one of an optical system for imaging a capture region, one or more mirrors of the optical system, and/or one or more lenses of the optical system, a stereo camera system, or one or more cameras of the stereo camera system, determining required adjustment measures and/or calibration measures in an automated fashion using the identified interchanged and/or misaligned at least one component as a starting point, wherein the required adjustment measures and/or calibration measures are for recalibrating the medical microscope to restore validity of calibration for the identified interchanged and/or misaligned at least one component, and wherein the recalibrating the medical microscope excludes calibration of a component external to the medical microscope, and performing the required adjustment measures and/or calibration measures.

2. The method as claimed in claim 1, wherein a calibration object with two-dimensional features and/or three-dimensional features is used to carry out the adjustment measures and/or calibration measures and said calibration object is arranged in a capture region of the medical microscope.

3. The method as claimed in claim 1, wherein the identifying the interchanged and/or misaligned at least one component is implemented at least partially manually, with at least one information item identifying the at least one interchanged and/or misaligned component being collected by way of a manual input.

4. The method as claimed in claim 1, wherein the identifying the interchanged and/or misaligned at least one component is implemented at least partially in automated fashion, with at least one information item identifying the at least one interchanged and/or misaligned component being read and/or retrieved out of the interchanged and/or misaligned component and/or from at least one controller of the medical microscope and/or from a service database.

5. The method as claimed in claim 1, wherein the required adjustment measures and/or calibration measures are at least partially determined by a lookup table, with adjustment measures and/or calibration measures that are required in each case following the interchange and/or misalignment being stored in the lookup table for interchangeable and/or adjustable components of the medical microscope.

6. The method as claimed in claim 1, wherein the required adjustment measures and/or calibration measures are at least partially retrieved from a database, with adjustment measures and/or calibration measures that are required in each case following the interchange and/or misalignment being stored in the database for interchangeable and/or adjustable components of the medical microscope.

7. The method as claimed in claim 1, wherein the required adjustment measures and/or calibration measures are at least partially determined by a trained artificial intelligence method.

8. The method as claimed in claim 1, further comprising displaying the determined required adjustment measures and/or calibration measures on a display device.

9. The method as claimed in claim 1, wherein at least some of the determined required calibration measures are performed in automated fashion.

10. The method as claimed in claim 1, wherein at least one calibration object is arranged in automated fashion in a capture region by an actuator system in order to carry out the determined required adjustment measures and/or calibration measures and/or wherein the medical microscope is controlled so that a capture region of the medical microscope captures at least one calibration object in order to carry out the determined required adjustment measures and/or calibration measures.

11. The method as claimed in claim 1, wherein the required adjustment measures and/or calibration measures are combined and/or optimized with one another in the case of a plurality of interchanged and/or misaligned components, in order to minimize a number and/or a scope of the measures.

12. The method as claimed in claim 1, further comprising collecting and/or recording data for anticipatory servicing in the medical microscope, with data for determining and/or optimizing the determination of the adjustment measures and/or calibration measures being evaluated, said data having been collected before, during and/or after the interchange and/or the misalignment of the at least one component.

13. The method as claimed in claim 1, further comprising capturing a respective state of the medical microscope before and after the interchange and/or misalignment, with associated image representations of at least one calibration object being captured by at least one camera of the medical microscope and with the required adjustment measures and/or calibration measures being determined by a trained artificial intelligence method, with the states captured before and after the interchange and/or the misalignment and the associated captured image representations being taken into account.

14. A medical microscope arrangement comprising:

a medical microscope with storable calibration data; and a data processing device comprising a computing device and a memory, the data processing device being configured to execute instructions stored on the memory to:

following an interchange and/or a misalignment of at least one component of the medical microscope, identify the interchanged and/or misaligned at least one component and/or to receive identifying information in relation to the interchanged and/or misaligned at least one component, the at least one component being at least one of an optical system for imaging a capture region, one or more mirrors and/or one or more lenses of the optical system, a stereo camera system, or one or more cameras of the stereo camera system, determine required adjustment measures and/or calibration measures in automated fashion using the identified at least one interchanged and/or misaligned component as a starting point, wherein the required adjustment measures and/or calibration measures are for recalibrating the medical microscope to restore validity of calibration for the identified interchanged and/or misaligned at least one component, and wherein the recalibrating the medical microscope excludes calibration of a component external to the medical microscope, and cause the determined required adjustment measures and/or calibration measures to be carried out.

* * * * *